United States Patent
Lampropoulos et al.

(10) Patent No.: US 7,470,256 B2
(45) Date of Patent: Dec. 30, 2008

(54) SELF-SUTURING ANCHOR DEVICE FOR A CATHETER

(75) Inventors: Fred P. Lampropoulos, Sandy, UT (US); Arlin Dale Nelson, Sandy, UT (US); D. Kent Backman, Salt Lake City, UT (US); Gregory R. McArthur, Sandy, UT (US); Thomas D. Stout, Salt Lake City, UT (US); Brian Stevens, Pleasant Grove, UT (US)

(73) Assignee: Merit Medical Systems, Inc.,, South Jordan, UT (US)

( * ) Notice: Subject to any disclaimer, the term of this patent is extended or adjusted under 35 U.S.C. 154(b) by 686 days.

(21) Appl. No.: 11/198,666

(22) Filed: Aug. 5, 2005

(65) Prior Publication Data

US 2006/0095009 A1    May 4, 2006

Related U.S. Application Data

(60) Provisional application No. 60/627,485, filed on Nov. 12, 2004, provisional application No. 60/623,502, filed on Oct. 29, 2004.

(51) Int. Cl.
*A61M 5/32* (2006.01)
(52) U.S. Cl. ..................................................... 604/180
(58) Field of Classification Search ......... 604/174–180, 604/116–117; 606/139–153, 130; 600/208, 600/227, 228, 229, 231–234, 236, 237
See application file for complete search history.

(56) References Cited

U.S. PATENT DOCUMENTS

| | | | |
|---|---|---|---|
| 2,669,231 A | 2/1954 | Fisher | |
| 4,221,215 A * | 9/1980 | Mandelbaum | .............. 604/327 |
| 4,372,073 A | 2/1983 | Goldman | |
| 4,717,385 A * | 1/1988 | Cameron et al. | ............. 604/174 |
| 4,869,719 A | 9/1989 | Hogan | ......................... 604/174 |
| 4,874,380 A | 10/1989 | Hesketh | ...................... 604/180 |
| 5,224,935 A | 7/1993 | Hollands | |
| 5,416,952 A | 5/1995 | Dodge | |

(Continued)

OTHER PUBLICATIONS

European Search Report, PCT/US2005/038910 dated Aug. 20, 2007, 8 pages.

(Continued)

*Primary Examiner*—Kenneth Bomberg
*Assistant Examiner*—Rebecca E Eisenberg
(74) *Attorney, Agent, or Firm*—Ryan D. Benson; Stoel Rives, LLP

(57) ABSTRACT

A self-suturing anchor device includes rotatable ring adapted to automatically deploy sutures to secure a catheter. The rotatable ring is utilized in connection with a ratchet mechanism which allows movement of the rotatable ring in a first direction while preventing movement of the rotatable ring in the opposite direction. The rotatable ring is also utilized in connection with a bearing member to facilitate smooth and efficient rotation of the rotatable ring. An extension saddle is utilized to provide a desired amount of displacement between suture securement points to minimize pivotal movement of the catheter. The rotatable ring is wider than its height to minimize kinking of the catheter tube and to relieve pressure when pressed between the patient and a support surface. In another embodiment, a plurality of scallops or other gripping members are utilized to facilitate easy gripping and rotation of the rotatable ring.

44 Claims, 7 Drawing Sheets

U.S. PATENT DOCUMENTS

| | | | |
|---|---|---|---|
| 5,911,229 | A | 6/1999 | Chodorow |
| 6,138,866 | A | 10/2000 | Lambelet, Jr. et al. |
| 6,554,297 | B2 | 4/2003 | Phillips et al. |
| 2001/0037119 | A1 | 11/2001 | Schmieding |
| 2002/0002324 | A1* | 1/2002 | McManus .................. 600/208 |
| 2002/0072713 | A1 | 6/2002 | Almond et al. |
| 2006/0095008 | A1 | 5/2006 | Lampropoulos et al. |

OTHER PUBLICATIONS

International Search Report and Written Opinion—Apr. 10, 2008.
International Search Report and Written Opinion—Jun. 14, 2006.
US Office Action for U.S. Appl. No. 11/535,454 dated Jul. 28, 2008.
US Office Action for U.S. Appl. No. 11/202,484 dated Jul. 29, 2008.
US Office Action for U.S. Appl. No. 11/532,056 dated Jul. 29, 2008.

* cited by examiner

SELF-SUTURING ANCHOR DEVICE FOR A CATHETER

CROSS-REFERENCE TO RELATED APPLICATIONS

This application claims the benefit of priority to U.S. Non-provisional patent application Ser. No. 11/082,170 entitled "Self-suturing Anchor Device a Catheter," filed on Apr. 16, 2005; which claims the benefit of priority to U.S. Provisional Patent Application No. 60/623,502, filed on Oct. 29, 2004, entitled "Self-suturing Anchor Device for a Catheter"; and to U.S. Provisional Patent Application No. 60/627,485, filed on Nov. 12, 2004, entitled "Self-suturing Anchor Device for a Catheter", the entire specifications of both applications are incorporated herein by reference.

BACKGROUND OF THE INVENTION

1. The Field of the Invention

Exemplary embodiments of the present invention relate to the field of catheters, and, more particularly, to a self-suturing anchor device for use with a catheter.

2. Background and Relevant Art

Catheters play an important role in the treatment and care of patients in modern medicine. In particular, catheters provide relatively unobtrusive access to remote portions of a patient's body, allowing desired procedures or treatments to be performed.

A wide variety of generalized and specialized catheters have been developed and refined for particular uses. For example, angioplasty catheters have been adapted to provide a safe and effective conduit for the delivery of a stent and/or balloon to a narrowing or blockage in a patient's artery or vein. Drainage catheters are configured to be inserted into a cavity adjacent or inside a patient's kidney, liver or other organ to drain excess fluid or infection from the cavity.

In addition, a number of devices and implements have been developed for use with catheters, to facilitate their effectiveness, or to overcome inherent difficulties associated with their use. For example, catheters that are designed to remain placed in a patient for long periods of time, such as for ongoing care or treatment of the patient, present a number of difficulties. Such catheters must be secured to the patient in a manner that minimizes movement of the catheter that could harm the patient, or otherwise interrupt proper functioning of the catheter.

Accordingly, one approach in the prior art has been to suture the catheter directly to the patient's skin. However, when a patient repositions himself/herself in bed, the catheter may pull at the suture site or bend the catheter. Another approach is to inflate a balloon associated with the distal end of the catheter inside the patient. However, at times an incoherent patient may attempt to withdraw or otherwise remove the catheter. This can cause injury to the catheter insertion site, or can interfere with proper operation of the catheter.

In view of these and other problems in the art, a number of devices have been a developed to secure a catheter in a manner that minimizes movement of the catheter, or minimizes interference with its proper operation. Typically, such devices include an adhesive layer to be secured to the patient with a small bore for accommodating the catheter and an adhesive strip to secure the catheter relative to the adhesive layer. Devices such as these are useful because they can be employed by a practitioner to secure the desired positioning of the catheter. Such devices, however, can be undesirable due at least in part to the fact that they typically cover or otherwise obstruct the catheter insertion site. This can make it difficult to identify infections, drainage, or other complications that may occur at the catheter insertion site. Furthermore, the devices can also obstruct cleaning of the insertion site, such that the site can only be cleaned by removing the anchor devices. Additionally, conventional anchor devices typically utilize a clip, or other securement member which typically is rigid or has a high profile when utilized to secure the catheter. As a result, the securement device can be uncomfortable if pressed against the patient by a chair, bed, or other object.

BRIEF SUMMARY OF THE INVENTION

The present invention relates to a self-suturing anchor device for a catheter. The self-suturing anchor device automatically secures the catheter without requiring the practitioner to manually suture the catheter to the self-suturing anchor device. The self-suturing anchor device has a securement mechanism which is adapted to be actuated by the user to automatically secure the catheter in a quick and efficient manner.

In one embodiment, a rotatable ring is provided in connection with the self-suturing anchor device to automatically secure the catheter. A pair of suture threads extends from the bottom of the rotatable ring. When a user pulls the threads in a rearward direction, the threads automatically secure a portion of the catheter associated with the bottom of the rotatable ring. The user can then rotate the rotatable ring in one of a clock-wise or a counter clock-wise direction. Rotation of the rotatable ring automatically secures the portion of the catheter positioned centrally within the rotatable ring.

The rotatable ring is utilized in connection with a ratchet mechanism. The ratchet mechanism allows movement of the rotatable ring in a first direction while preventing movement of the rotatable ring in the opposite direction. As a result, the rotational position of the rotatable ring is secured against movement in a direction that would result in loosening of the sutures. When the user rotates the rotatable ring to deploy, secure, and/or tighten the sutures relative to the catheter, inadvertent movement of the rotatable ring does not result in loosening of the sutures. Additionally, where the tension on the sutures decreases due to factors such as the natural loosening of the fibers of the suture, the user can easily ratchet the rotatable ring an additional amount to return the sutures to a desired degree of tension.

The rotatable ring can be utilized in connection with a bearing member to facilitate smooth and efficient rotation of the rotatable ring. In one embodiment, the rotatable ring comprises a stationary base and a rotatable outer ring. The stationary base is secured to the adhesive layer which is adhered to the patient. The rotatable outer ring circumscribes the stationary base allowing the outer ring to be rotated by the user relative to the stationary base. The bearing member is positioned between the stationary base and the rotatable outer ring. The bearing properties of the bearing member facilitate movement of the rotatable outer ring relative to the stationary base. In one embodiment, the bearing member includes solid surface bearing properties. In another embodiment, the bearing member comprises a bearing mechanism such as a fluid type, or roller bearing surface mechanism.

The anchor device of the present invention can include a variety of types and configurations of features to facilitate simple and effective securement of the catheter. For example, in one embodiment an extension saddle is utilized to provide a desired amount of displacement between suture securement points to minimize pivotal movement of the catheter. In another embodiment, the rotatable ring is wider than its height to minimize kinking of the catheter tube and to relieve pressure when pressed between the patient and a support surface. In another embodiment, a plurality of scallops or other gripping members are utilized to facilitate easy gripping and rotation of the rotatable ring. In another embodiment, a removable lid is provided which can cover the catheter insertion point such as when the user takes a shower or during sleep.

Additional embodiments described herein relate to variations on the anchor device, and different methods for drawing the suture loops about the catheter. According to the present invention, deployment of the securement devices can be effectuated quickly and effectively with minimal training and/or effort. Furthermore, the present invention allows a practitioner to easily view the treatment site on the patient, thereby allowing the practitioner to treat or clean the site as needed without having to release or remove the catheter from the anchor device.

Additional features and advantages of exemplary embodiments of the invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention extends to a self-suturing anchor device for a catheter. The self-suturing anchor device automatically secures the catheter without requiring the practitioner to manually suture the catheter to the self-suturing anchor device. The self-suturing anchor device has a securement mechanism which is adapted to be actuated by the user to automatically secure the catheter in a quick and efficient manner.

Figure 1:
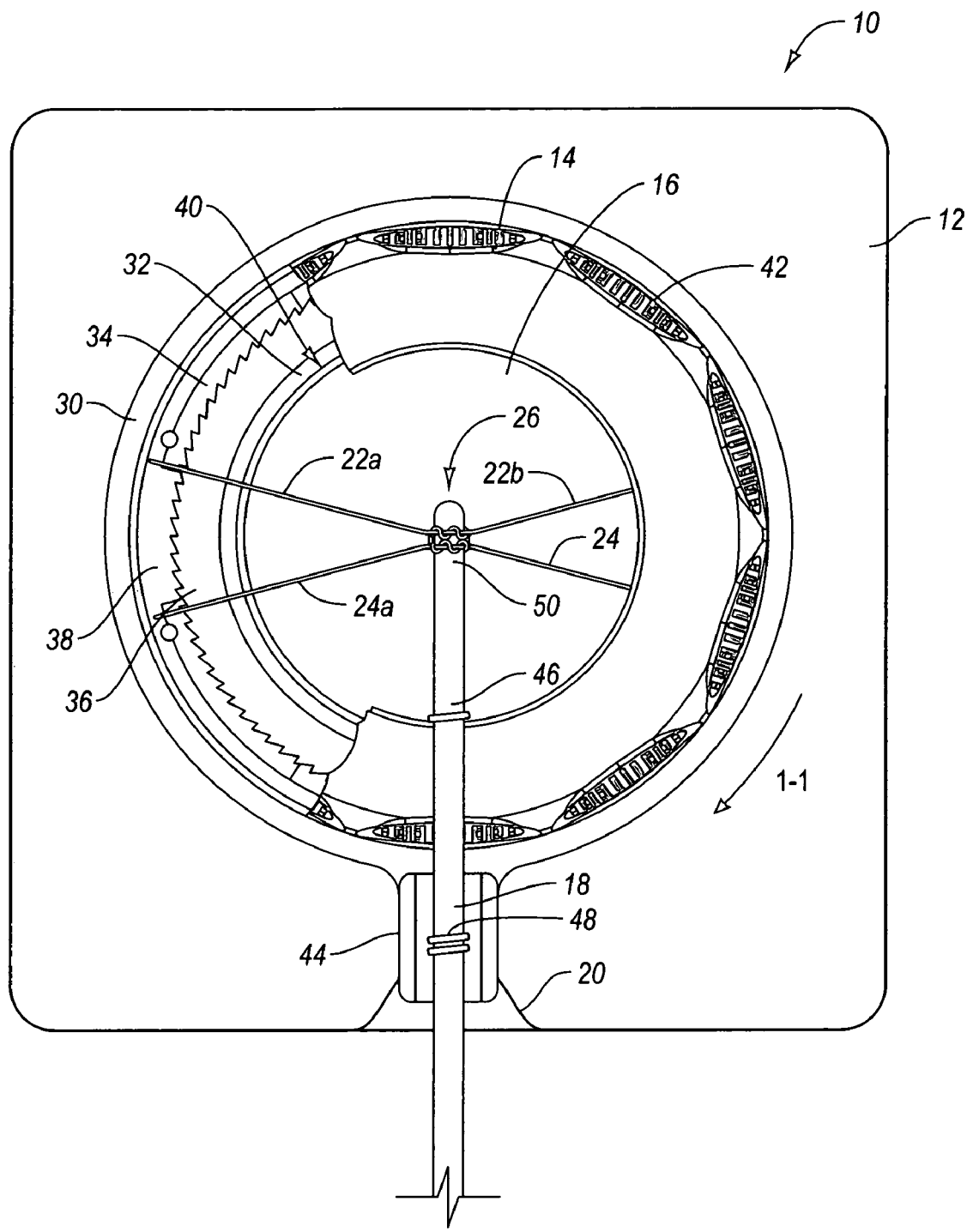
FIG. 1 is a partial cross-sectional top view of an anchor device illustrating a catheter being secured to a patient.

FIG. 1 is a partial cross-sectional top view of an anchor device 10 illustrating anchor device 10 securing a catheter 18 to a patient according to one embodiment of the present invention. Anchor device 10 is adapted to be used with the catheter 18 that has been inserted into a patient. Anchor device 10 minimizes movement of catheter 18 that could result in pressure, discomfort, displacement, or tearing at a catheter insertion site 26. Anchor device 10 is configured to automatically deploy one or more sutures to quickly and efficiently secure the catheter 18.

In the illustrated embodiment, anchor device 10 includes an adhesive sheet 12, a rotatable ring 14, a center aperture 16, a first suture 20, a second suture 22, and a third suture 24. Adhesive sheet 12 is configured to be secured to the skin of the patient proximate catheter insertion site 26. Adhesive sheet 12 provides effective and flexible securement of anchor device 10 to the patient without causing discomfort or injury to the patient. Center aperture 16 surrounds the catheter insertion site 26. Center aperture 16 allows a user to see and access catheter insertion site 26. Center aperture 16 permits the practitioner to access catheter insertion site 26 without manipulating or removing adhesive sheet 12.

Rotatable ring 14 is coupled to adhesive sheet 12 circumscribing center aperture 16. Rotatable ring 14 is configured to be actuated by a practitioner to automatically secure the catheter 18 to minimize inadvertent or unintentional movement of catheter 18. First suture 20, second suture 22, and third suture 24 are utilized in connection with rotatable ring 14. At least one of first suture 20, second suture 22, and third suture 24 are configured to be deployed by actuation of rotatable ring 14 to automatically secure catheter 18. As the user rotates rotatable ring 14, at least one of sutures 20, 22, and 24 are deployed to automatically secure catheter 18. In the illustrated embodiment, a user rotates rotatable ring 14 in the direction of directional arrows 1-1 (clockwise direction) to deploy at least one of first suture 20, second suture 22, and third suture 24. In the illustrated embodiment, first suture 20, second suture 22, and third suture 24 have been deployed.

First suture 20 secures catheter 18 at first securement point 46 and second securement point 48. Second suture 22 and third suture 24 secure catheter 18 at third securement point 50. An extension saddle 44 is provided at the bottom of rotatable ring 14. Both ends of first suture 20 are threaded to extension saddle 44. When the user pulls both ends of suture 20 to actuate first suture 20, first suture 20 automatically secures catheter 18 at first securement point 46. Subsequent to deployment of first suture 20, a user ties suture 20 at second securement point 48. Deployment of first suture 20 will be discussed in greater detail in FIG. 4. Extension saddle 44 provides a desired amount of displacement between first securement point 46 and second securement point 48. The amount of displacement between first securement point 46 and second securement point 48 minimizes twisting of catheter tube 18 that could otherwise result in injury at the catheter insertion site.

In the illustrated embodiment, second suture 22 and third suture 24 provide two points of securement lateral to third securement point 50. As a result, movement of catheter 18 in a lateral direction or in a forward or rearward direction is prevented. In the event that catheter 18 is inadvertently pulled in a rearward direction second suture 22 and third suture 24 inhibits movement of catheter 18. Similarly, in the event that catheter 18 is bumped or otherwise manipulated in a lateral direction, the two points of securement on each lateral side of third securement point 50 minimize lateral movement, twisting, or other manipulation of catheter 18 at catheter insertion point 26. As a result, discomfort, tearing, displacement, or injury at the catheter insertion point 26 resulting from inadvertent movement of catheter 18 is minimized.

In the illustrated embodiment, rotatable ring 14 includes a ratchet mechanism and a bearing member. Rotatable ring 14 comprises a rotatable outer ring 30, base 32, a bearing member 34, a ratchet ring 36, a rotatable ratchet member 38, and a suture storage channel 40. Base 32 is stationarily secured to adhesive sheet 12. Base 32 provides an implement for supporting the other components of rotatable ring 14. Rotatable ring 30 is positioned adjacent to and circumscribing base 32. Rotatable ring 30 is configured to be rotated by the user relative to base 32 to deploy second suture 22 and third suture 24.

Bearing member 34 is positioned between base 32 and rotatable outer ring 30. Bearing member 34 has bearing properties to minimize the friction between base 32 and rotatable outer ring 30 to facilitate rotation of rotatable outer ring 30 relative to base 32. In the illustrated embodiment, bearing member 34 comprises solid surface bearing material providing sliding surface bearing properties. In one embodiment, bearing member 34 comprises one or more of acetyl, high molecular weight polyethylene, lubricous plastic, Delria®, Nylon filled with lubricant, other solid surface member, polymer material, and/or antifriction material. In the illustrated embodiment, bearing member 34 is configured to be coupled to rotatable outer ring 30 such that bearing member 34 rotates with rotatable outer ring 30. The ends of second suture 22 and third suture 24 are configured to be secured to bearing member 34. When rotatable outer ring 30 is rotated, bearing member 34 moves about the circumference of base 32 and sutures 22 and 24 are foreshortened. As a result, sutures 22 and 24 are deployed.

Ratchet ring 36 is secured to base 32 such that ratchet ring 36 is stationary relative to the adhesive sheet. Ratchet ring 36 includes a plurality of teeth or ramp portions which are configured to interact to maintain the rotational position of rotatable outer ring 30. Rotatable ratchet member 38 is coupled to rotatable outer ring 30. Rotatable ratchet member 38 includes a plurality of teeth which cooperatively interact with the teeth of ratchet ring 36. The cooperative interaction between rotatable ratchet member 38 and ratchet ring 36 allow movement of rotatable outer ring 30 in only the direction of directional arrows 1-1. As a result, rotatable ratchet member 38 and ratchet ring 36 prevent rotation of rotatable outer ring 30 in a counter clockwise direction securing the rotational position of rotatable outer ring 30. As a result, the inadvertent movement of rotatable outer ring 30 that could result in loosening of sutures 22 and 24 is prevented. In the illustrated embodiment rotatable ratchet member 38 and ratchet ring 36 comprise a ratchet mechanism.

In the illustrated embodiment, suture storage channel 40 is provided on the inside diameter of base 32. Sutures 20, 22, and 24 are configured to be positioned in suture storage channel 40 previous to actuation of rotatable ring 14. As a result, previous to deployment, sutures 20, 22, and 24 are safely secured in suture storage channel 40 such that sutures 20, 22, and 24 are completely contained. When anchor device 10 is being placed on the patient, sutures 20, 22, and 24 are safely contained in the suture storage channel 40 preventing tangling of sutures 20, 22, and 24 or other interference with aspects of the procedure being performed. As the user begins to retract the ends of suture 20 in a rearward direction, suture 20 is deployed from suture storage channel 40. As the user actuates rotatable ring 14 by rotating rotatable outer ring 30, sutures 22 and 24 are deployed from their positioning in sutures storage channel 40. In one embodiment, a plurality of adhesive layers are provided between the sutures to maintain and secure the position of the sutures in the suture storage channel before deployment of the sutures. Deployment of sutures 20, 22, and 24 will be discussed in more detail in FIGS. 4 and 5.

In the illustrated embodiment, rotatable outer ring 30 includes a plurality of scallops 42. Scallops 42 provide variability in the relief of the upper surface of rotatable outer ring 30. As a result, the user can more easily grasp the rotatable outer ring 30 for actuation of rotatable ring 14 and actuation of sutures 22 and 24. Scallops 42 comprise slight concavities on the surface of rotatable outer ring 30. As a result, scallops do not snag articles and materials that come in contact with rotatable outer ring 30. This minimizes interference with the procedure being performed while minimizing inadvertent interruption with anchor device 10 during use. As will be appreciated by those skilled in the art, a variety of types and configurations of gripping members or anti-friction mechanisms can be utilized with rotatable outer ring 30 without departing from the scope and spirit of the present invention.

Figure 2:
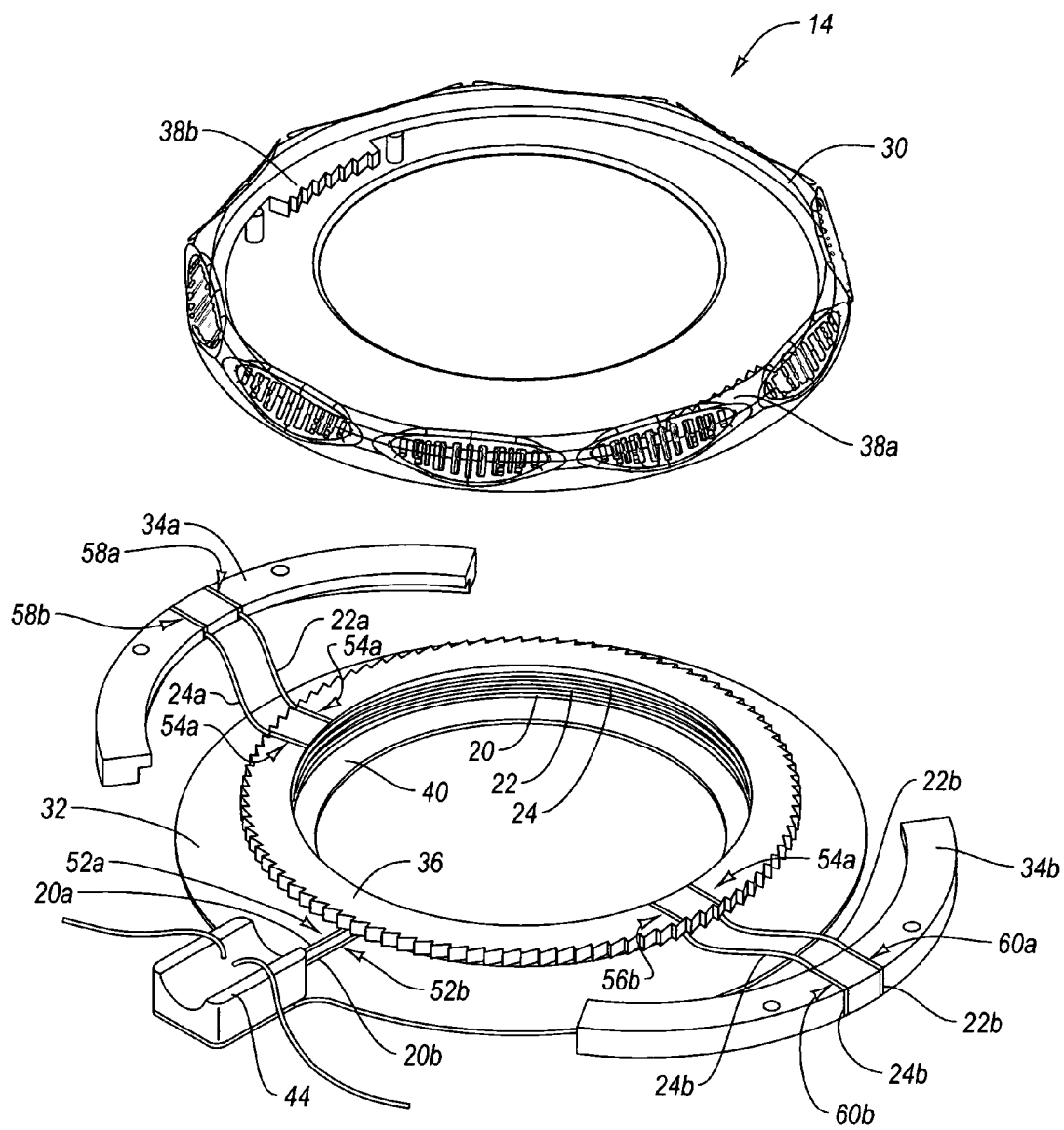
FIG. 2 is an exploded view of a rotatable ring of the anchor device depicting a ratchet mechanism.

FIG. 2 is an exploded view of rotatable ring 14 of anchor device 10 depicting a ratchet mechanism. In the illustrated embodiment, rotatable outer ring 30 and bearing members 34a, b are shown separated from base 32. Rotatable ratchet members 38a, b are integrally coupled to rotatable outer ring 30. A pair of pin members are positioned beneath each of rotatable ratchet members 38a, b. The pin members are configured to be positioned in bearing members 34a, b to secure bearing members 34a, b and to rotatable outer ring 30.

Bearing members 34a, b are configured to be positioned between rotatable outer ring 30 and base 32. Bearing members 34a, b contact base 32 beneath ratchet ring 36 such that bearing members 34a, b do no contact the teeth of ratchet ring 36. Similarly, bearing members 34a, b contact rotatable outer ring 30 beneath rotatable ratchet members 38a, b such that bearing members 34a, b do not contact the teeth of rotatable ratchet members 38a, b. As a result, bearing members 34a, b do not interfere with the cooperative engagement between ratchet members 38a, b and ratchet ring 36.

A lip on each of bearing members 34a, b extends inwardly beneath ratchet ring 36. When rotatable outer ring 30 is secured to bearing members 34a, b, the lateral positioning of bearing members 34a, b secures both bearing members 34a, b and rotatable outer ring 30 to base 32. Additionally, the positioning of bearing members 34a, b secures ratchet members 38a, b in cooperative engagement with ratchet ring 36.

As will be appreciated by those skilled in the art, a variety of types and configurations of bearing members can be utilized without departing from the scope and spirit of the present invention. For example, in one embodiment a circular bearing member is utilized in place of two bearing member segments. In another embodiment, one or more bearing members are integrally coupled to the rotatable outer ring. In yet another embodiment one or more bearing members are integrally coupled to the ratchet members. In yet another embodiment, a liquid bearing mechanism is utilized. In another embodiment, a roller bearing mechanism is utilized.

In the illustrated embodiment, the path of sutures 20, 22, and 24 relative to sutures storage channel 40 previous to deployment is depicted. Sutures 20, 22 and 24 are looped such that they are positioned inside suture storage channel 40. As a result, when the practitioner secures the anchor device to the patient, the practitioner does not need to manage the positioning of sutures 20, 22, and 24. Suture storage channel 40 also maintains the particular desired loop formation of sutures 20, 22, and 24 ensuring proper operation and/or deployment of sutures 20, 22, and 24.

In the illustrated embodiment, first suture channels 52a, b are positioned through base 32 and exiting at extension saddle 44. First suture 20 is configured to be positioned through first suture channels 52a, b such that the ends of first suture 20 extend from extension saddle 44. The extension of the ends of first suture 20 from the extension saddle 44 allows a user to grasp the ends of first suture 20 to actuate first suture 20.

Second suture channels 54a, b and third suture channels 56a, b are positioned through ratchet ring 36 and base 32. Bearing member suture channels 58a, b and 60a, b are positioned through bearing members 34a, b. The second suture 22 and third suture 24 are threaded through suture channels 54a, b; 56a, b; 58a, b; and 60a, b. In more particular, first end 22a of second suture 22 is threaded through second suture channel 54a and bearing member channel 58a, and is secured at the exterior of bearing member 34a. Second end 22b of second suture 22 is threaded through second suture channel 54b, through bearing member channel 60a, and is secured at the exterior of bearing member 34b. First end 24a of third suture 24 is threaded through third suture channel 56a, through bearing member channel 58b and is secured at the exterior of bearing member 34a. Second end 24b of third suture 24 is threaded through third suture channel 56b, through bearing member channel 60b, and is secured at the exterior of bearing member 34b.

Base 32 and ratchet ring 34 are stationary relative to the rotatable outer ring 30. As a result, second suture channel 54a, b and third suture channel 56a, b remain stationary during operation of rotatable ring 14. Bearing members 34a, b rotate in connection with rotatable outer ring 30. As a result, bearing member suture channels 58a, b and 60a, b rotate in connection with rotation of rotatable outer ring 30 and bearing member 34a, b. When bearing members 34a, b rotate in a clockwise direction, the ends of sutures 22 and 24 are drawn around the outside diameter of base 32 beneath ratchet ring 36. As a result, the length of first and second sutures 22 and 24 inside suture storage channel 40 is shortened. As the length of first and second sutures 22 and 24 inside suture storage channel 40 is shortened, the loops of sutures 22 and 24 become smaller such that they can no longer fit in suture storage channel 40. This results in automatic deployment of the loops of sutures 22 and 24 from suture storage channel 40.

As will be appreciated by those skilled in the art, a variety of types and configurations of sutures and suture storage channels can be utilized without departing from the scope and spirit of the present invention. For example, in one embodiment both ends of each suture exit through suture channels in the same sidewall of the base of the rotatable ring. In another embodiment, the suture channels comprise bores rather than slots. In another embodiment, the ends of the suture are integrally affixed to the bearing members. In yet another embodiment, four independent sutures are utilized in the place of the first and second suture. In the illustrated embodiment, the suture storage channel is shown without a retention flange for the sake of clarity.

Figure 3A:
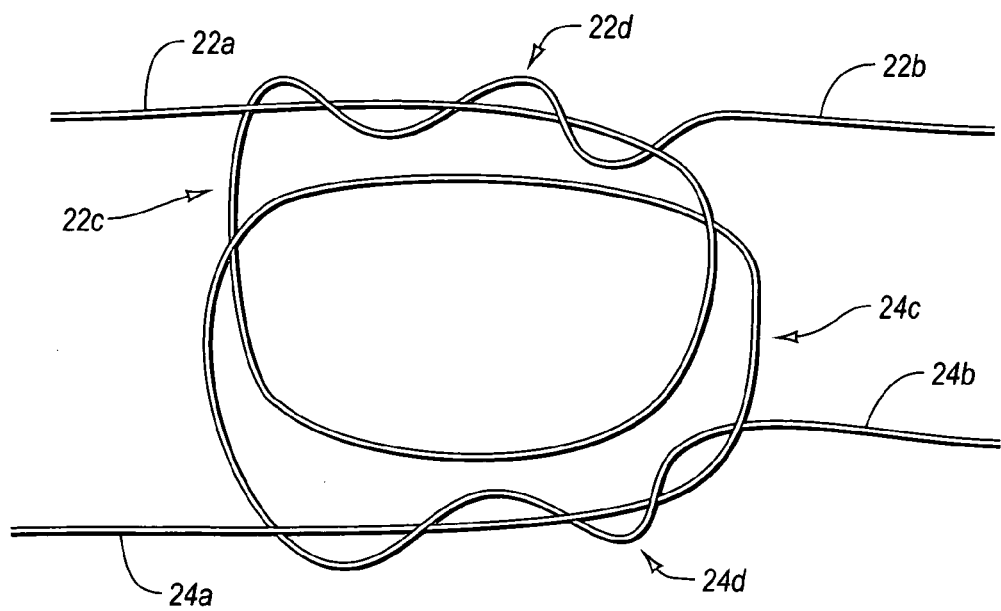
FIG. 3 illustrates the configuration of sutures of the anchor device utilized to secure the catheter.
Figure 3B:
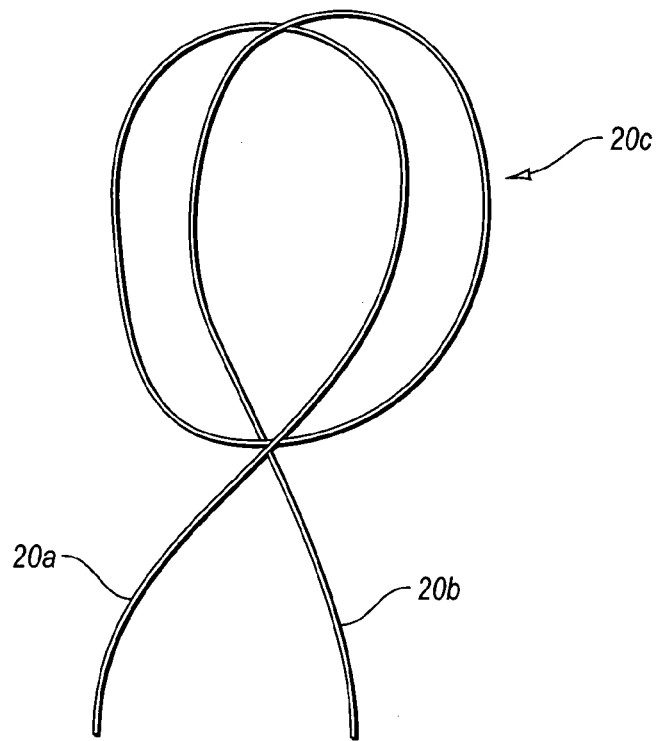

FIG. 3 illustrates the loop configuration of sutures 20, 22, and 24 utilized to secure a catheter. In the illustrated embodiment, first suture 20 includes a first end 20a, a second end 20b, and a double loop portion 20c. Double loop portion 20c of first suture 20 is configured to form a clove hitch when secured about a catheter. Previous to deployment from the suture storage channel 40 (see FIG. 2) the double loop configuration of double loop portion 20c is adapted to be wide enough to fit within the suture storage channel 40 depicted in FIG. 2.

In the illustrated embodiment, second suture 22 includes a first end 22a, a second end 22b, a loop portion 22c, and a double wrapped portion 22d. As previously discussed, first end 22a is configured to be threaded through a plurality of suture channels and be secured adjacent a bearing member. Similarly second end 22b is configured to be threaded through a plurality of suture channels and be secured adjacent a bearing member. Previous to deployment, loop portion 22c is configured to fit easily within the stuture storage channel 40 depicted in FIG. 2. Subsequent to deployment, loop portion 22c is tightened around the catheter. The double wrapped portion 22d is configured to maintain the tightened configuration of loop portion 22c subsequent to deployment of second suture 22.

In the illustrated embodiment, third suture 24 includes a first end 24a, a second end 24b, a loop portion 24c, and a double wrapped portion 24d. As previously discussed, first end 24a is configured to be threaded through a plurality of suture channels and be secured adjacent a bearing member. Similarly second end 24b is configured to be threaded through a plurality of suture channels and be secured adjacent a bearing member. Previous to deployment, loop portion 24c is configured to fit easily within the stuture storage channel 40 depicted in FIG. 2. Subsequent to deployment, loop portion 24c is tightened around the catheter. The double wrapped portion 24d is configured to maintain the tightened configuration of loop portion 24c subsequent to deployment of third suture 24.

The loop portions 22c and 24c of second suture 22 and third suture 24 are adapted to overlap with one another. The overlapping configuration of second suture 22 and third suture 24 is configured to provide cooperative securement of a catheter subsequent to deployment of second suture 22 and third suture 24. As will be appreciated by those skilled in the art, a variety of types and configurations of sutures and suture loops can be utilized without departing from the scope and spirit of the present invention. For example, in one embodiment both ends of second suture are positioned on one lateral side while both ends of third suture are positioned on the opposite lateral side. In another embodiment, the loops of second suture and third suture are coupled to one another such that the sutures are centered during closure of the loop portions.

Figure 4:
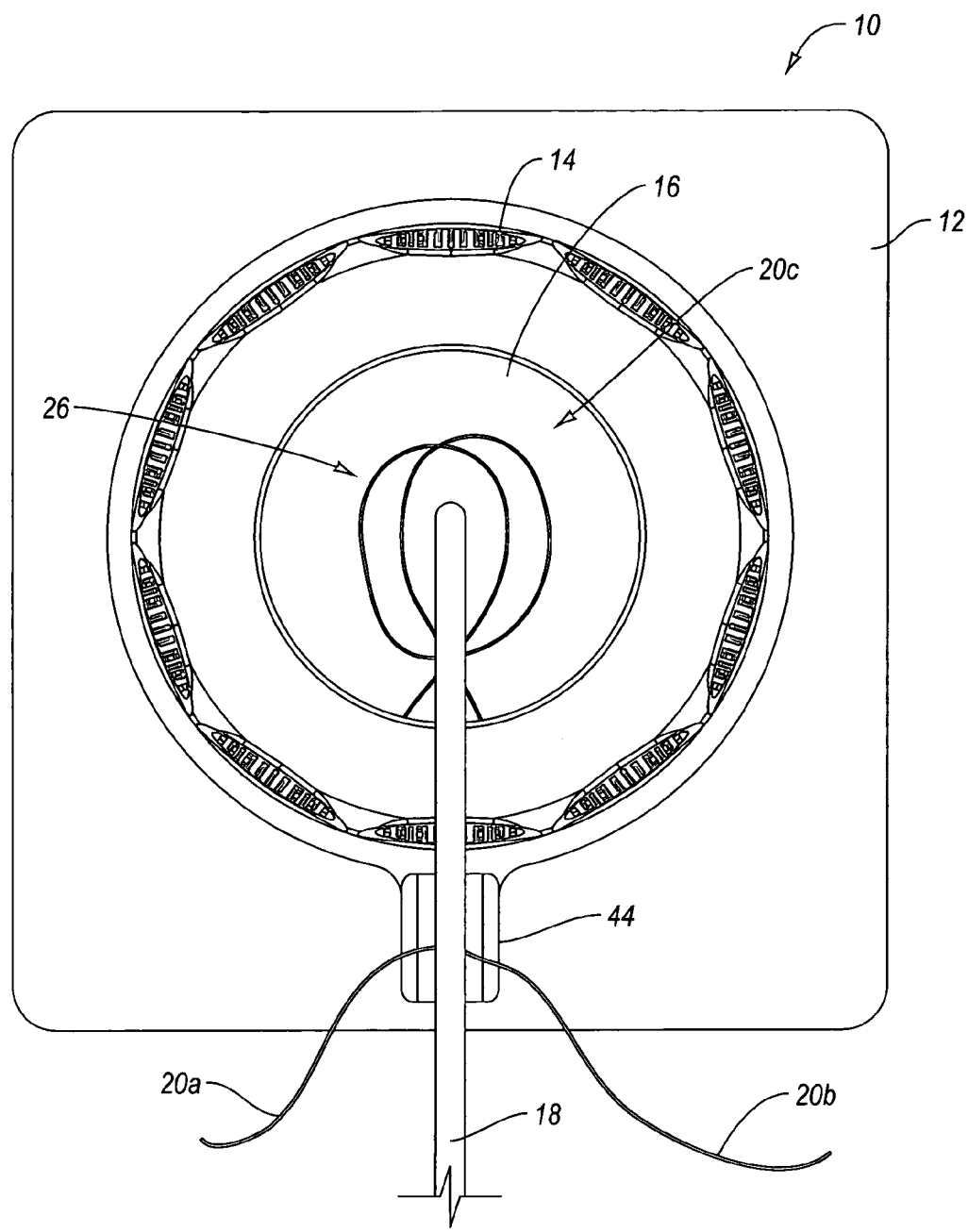
FIG. 4 is a top view of the anchor device of FIG. 1 illustrating deployment of a first suture.

FIG. 4 is a top view of the anchor device 10 illustrating deployment of first suture 20. To deploy first suture 20 a user grasps first end 20a and second end 20b and retracts in a rearward direction. The double loop portion 20c of first suture 20 is deployed as first end 20a and second end 20b are pulled in a rearward direction. Tensioning occurs as first end 20a and second end 20b are retracted further in the distal direction. In the illustrated embodiment, both the first loop and second loop of the double loop portion 20c have been deployed but have not substantially tightened around catheter 22. The first loop and second loop of double loop portion 20c are configured to encircle catheter 18.

In the illustrated embodiment, the double loop clove-hitch configuration of first suture 20 secures catheter 18 to rotatable ring 14 at a first securement point 46 (see FIG. 1). By maintaining the tension on first end 20a and second end 20b, first suture 20 retains catheter 18 against rotatable ring 14. Once first suture 20 is tightened about catheter 18 at first securement point 46 (see FIG. 1), first end 20a and second end 20b are tied to catheter 18 at second securement point 48 at extension saddle 44 (see FIG. 1).

As will be appreciated by those skilled in the art, the time required to secure catheter 18 utilizing first suture 20 can be as little as a few seconds. Not only is time saved in comparison to conventional techniques, but the steps of securing catheter 18 utilizing first suture 20 is conceptually simple, and readily conducted by a surgeon, by an assisting nurse, or other practitioner.

As will be appreciated by those skilled in the art, a variety of types and configurations of mechanisms for securing the catheter can be utilized without departing from the scope and spirit of the present invention. In one embodiment, the securement of the catheter utilizes a triple loop clove-hitch configuration. In another embodiment, the securement of catheter utilizes two double loop clove-hitch configurations from a first and second suture. In another embodiment, the suture secures the catheter utilizing an arrangement other than a clove-hitch loop. In yet another embodiment, the anchor device includes two or more resilient pockets from which multiple sutures can be deployed to secure the catheter against the rotatable ring 14.

Figure 5:
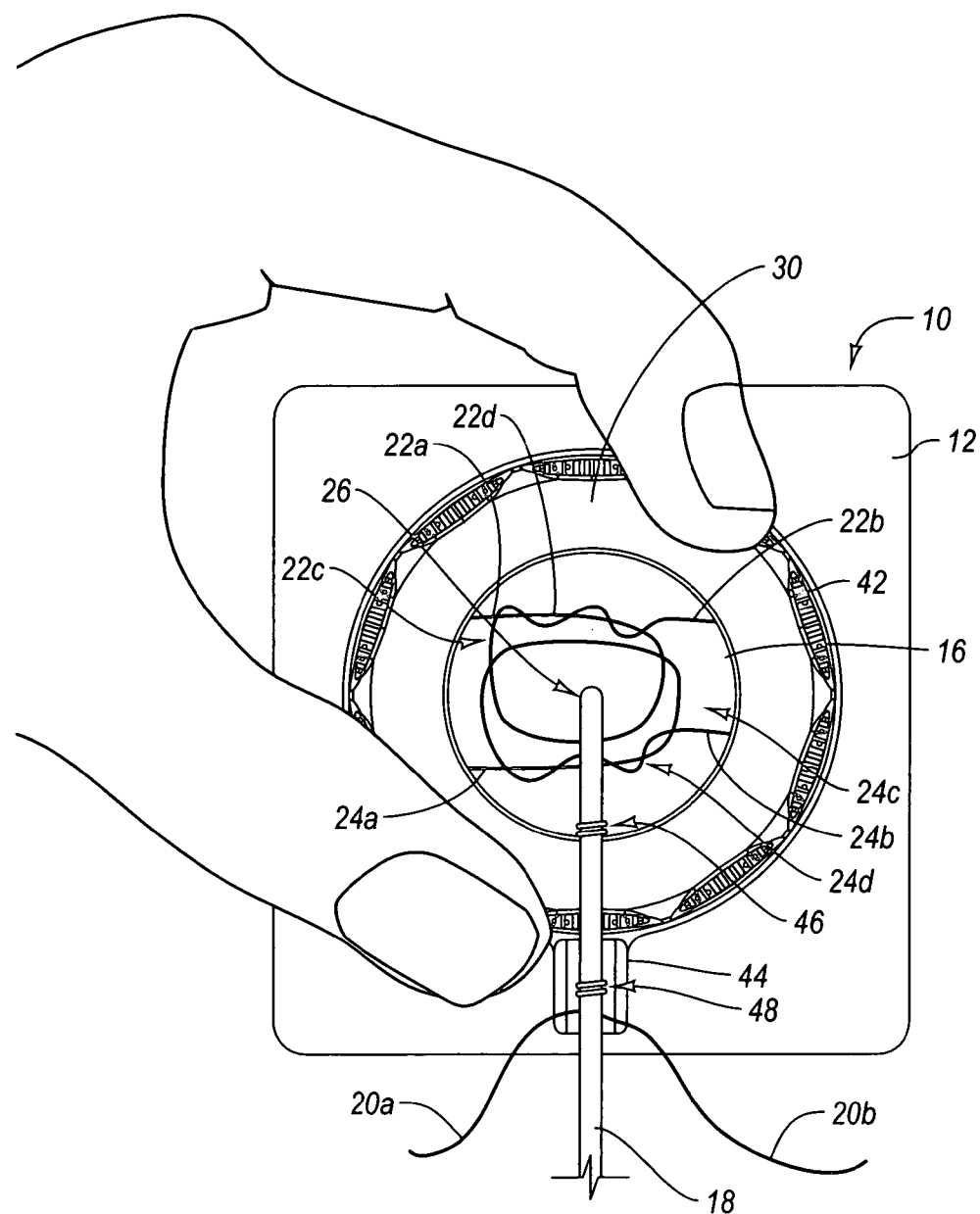
FIG. 5 is a top view of the anchor device of FIG. 1 illustrating deployment of a second suture and a third suture subsequent to securement of the first suture.

FIG. 5 depicts deployment of second suture 22 and third suture 24 to secure catheter 18 proximate catheter insertion site 26. To actuate sutures 22 and 24, the practitioner rotates rotatable outer ring 30 of rotatable ring 14. In the illustrated embodiment, rotatable ring 14 includes a rotatable outer portion of the ring and a stationary base 32. The practitioner rotates rotatable ring 14 in the clockwise direction, for example, approximately $\frac{1}{8}^{th}$ of a turn or 45 degrees. This rotation causes a portion of second suture 22 and third suture 24 to deploy from within suture storage channel 40.

Rotation of rotatable outer ring 30 results in movement of both bearing members (not shown). Because the one end of both second suture 22 and second suture 24 are secured to a bearing member (not shown) on both sides of rotatable ring 14, rotation of the rotatable outer ring 30 pulls the ends of both sutures around the outer circumference the base of rotatable ring 14. As a result, ends 22a and 22b of second suture 22 are pulled in opposite directions. Similarly, ends 24a and 24b of third sutures 24 are pulled in opposite directions. As a result, loop portions 22c and 24c are tightened without exerting undue pressure on catheter 18 or catheter insertion point 26.

As will be appreciated by those skilled in the art, a variety of types and configurations of mechanisms can be utilized in connection with deployment of the second and third sutures according to the present invention. For example, in one embodiment a slidable engagement mechanism such as a clip, ring, or preformed loop is utilized to form the loops of the first and second sutures. In another embodiment, a single suture is utilized in place of the second and third sutures. In yet another embodiment, three or more sutures are deployed during rotation of the rotatable ring.

As will be appreciated by those skilled in the art, the amount of time required to deploy second and third sutures 22 and 24 by actuating rotatable ring 14 is mere seconds. Additionally, as second and third sutures 22 and 24 are tightened about catheter 18 (as depicted in FIG. 1), the ratchet mechanism maintains securement of second and third sutures 22 and 24 about catheter 18. The ratchet mechanism also allows the user to tighten sutures 22 and 24 subsequent to any natural loosening of the suture thread.

Figure 6:
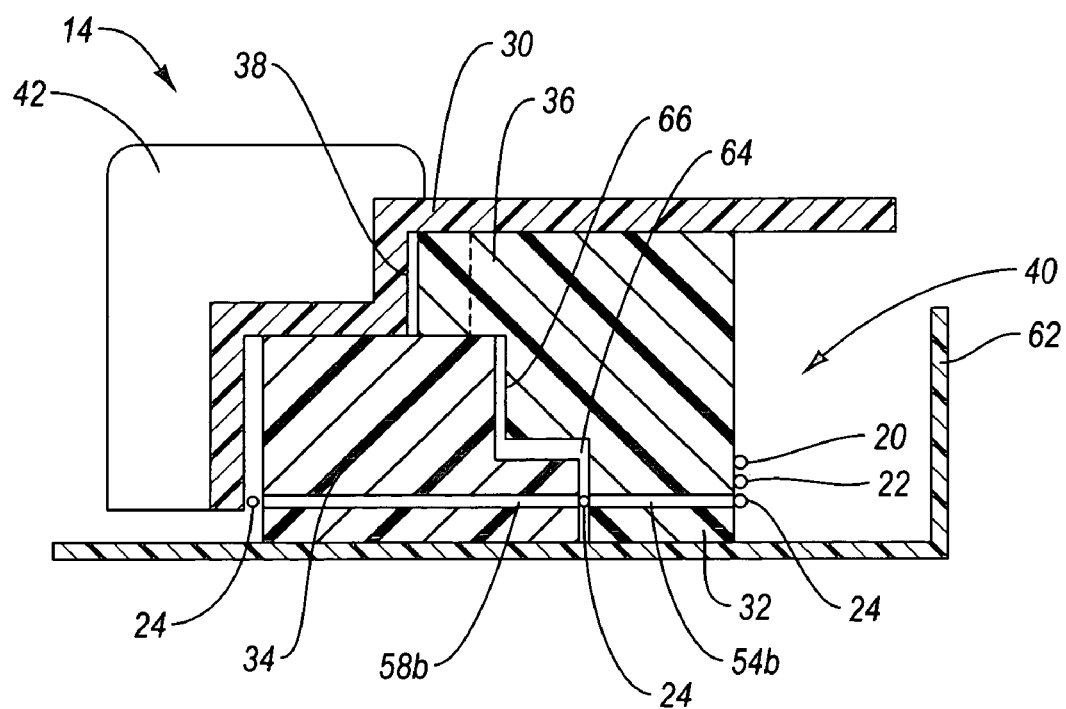
FIG. 6 is a cross-sectional side view of a portion of the rotatable ring illustrating a bearing member of the rotatable ring.

FIG. 6 is a cross-sectional side view of a portion of the rotatable ring 14 illustrating a bearing member 34 of the rotatable ring 14. In the illustrated embodiment, bearing member 34 is positioned between rotatable outer ring 30 and base 32. Base 32 includes a horizontal base member and an upright member. Ratchet ring 36 is integrally coupled to the upright member of base 32. Bearing member 34 is positioned on top of the horizontal member of base 32 and adjacent the upright member of base 32. Additionally, the top surface of bearing member 34 is positioned beneath ratchet ring 36. Bearing member 34 contacts the upright member of base 32 at interface 66. The profile of bearing member 34 and the upright member of base 32 results in the formation of slot 64. Slot 64 is configured to accommodate a suture (suture 24 in the illustrated embodiment) as bearing 34 moves around the circumference of base 32.

Rotatable outer ring 30 is positioned above and on the outside diameter of rotatable ring 14. Rotatable outer ring 30 is the portion of rotatable ring 14 that is grasped by the user to actuate rotatable ring 14. In the illustrated embodiment, the bottom surface of rotatable outer ring 30 is secured to bearing member 34. Rotatable ratchet member 38 is positioned above bearing member 34 and in contact with ratchet ring 36. As the user rotates rotatable outer ring 30, the teeth of rotatable ratchet member 38 slip in a counter clockwise direction past the teeth of ratchet ring 36. The teeth of ratchet ring 36 and ratchet member 38 cooperatively interact to prevent movement of the teeth of ratchet member 38, and thus rotatable outer ring 30, in a counterclockwise direction.

In the illustrated embodiment, sutures 20, 22, and 24 are depicted in suture storage channel 40. A flange 62 is secured to base 32. Flange 62 is positioned laterally inward from sutures 20, 22 and 24. Flange 62 maintains the position of sutures 20, 22, and 24 in suture storage channel 40 until deployment of sutures 20, 22, and 24. As sutures 20, 22, and 24 deploy and the loop portions of sutures 20, 22, and 24 become smaller, sufficient force is exerted on flange 62 to bend flange 62 inwardly. Additionally, as sutures 20, 22, and 24 deploy, flange 62 pushes sutures 20, 22, and 24 in an upward direction while bending inwardly. The upward movement of sutures 20, 22, and 24 facilitates the positioning of sutures 22 and 24 around catheter 18 (see FIG. 1) at a desired degree of displacement from the patient's skin. This facilitates cleaning of the catheter insertion site without interference of sutures 22 and 24.

As will be appreciated by those skilled in the art, a variety of types and configurations of rotatable rings and bearing members can be utilized without departing from the scope and spirit of the present invention. For example, the configuration and number of contact surfaces between the bearing members and rotatable rings can vary. In another embodiment, the bearing member includes ratchet surfaces that interact with one or more surfaces of the base and/or rotatable outer ring.

Figure 7:
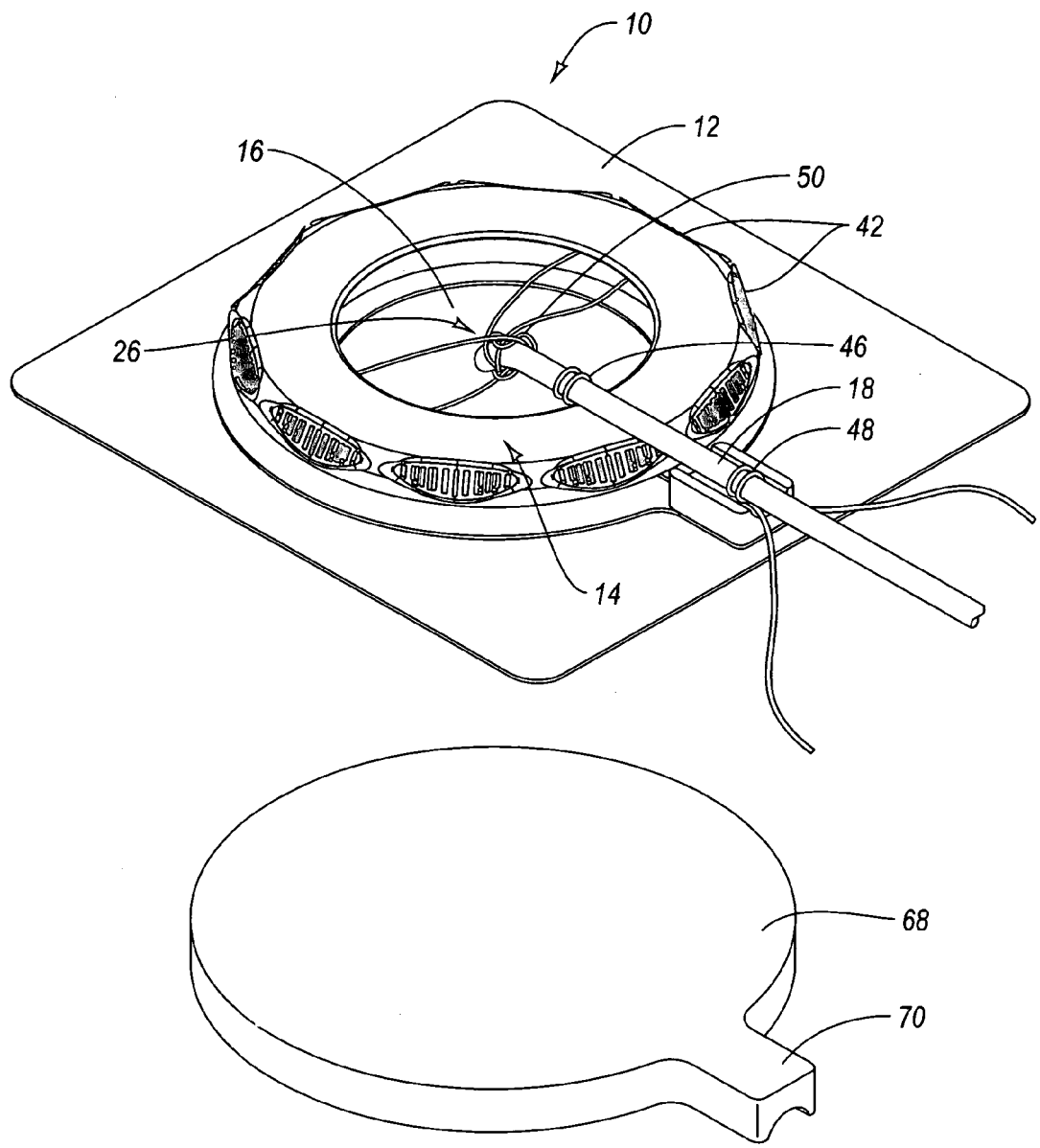
FIG. 7 is a perspective view of the anchor device of FIG. 1 and a removable lid for covering the center aperture and catheter insertion side.

FIG. 7 is a perspective view of the anchor device 10 of FIG. 1 and a removable lid 68 for covering center aperture 16 and catheter insertion site 26. In the illustrated embodiment, removable lid 68 is configured to provide protection to the catheter insertion site 26 from environmental interference. For example, in the event that a patient desires to take a shower, removable lid 68 can be placed over rotatable ring 14 to prevent the inflow of water or inadvertent injury to the catheter insertion site 26. This allows for continued use and securement of the catheter 18 while minimizing the potential for injury or interference with proper operation of the catheter insertion site 26.

In the illustrated embodiment, the rim of the removable lid 68 is configured to fit over the rotatable ring 14 to secure the removable lid 68 relative to the anchor device 10. An extension member 70 having an inner channel is provided to permit passage of catheter 18 to the exterior of the lid while permitting sealing and protection of center aperture 16.

As will be appreciated by those skilled in the art, a variety of types and configurations of removable lids can be utilized without departing from the scope and spirit of the present invention. For example, in one embodiment, the removable lid can be configured to be utilized the majority of the usage time of the anchor device. Alternatively, the use of the removable lid can be limited to the occasional situation when extra care or caution is deemed necessary to prevent injury to the catheter insertion site. In one embodiment, the removable lid is clear to permit observation of the catheter insertion site when the removable lid is positioned over the rotatable ring. In another embodiment, the removable lid is secured to the anchor device with a lanyard or other securement device when the removable lid is not in operation. This assures that the removable lid will be readily accessible in the event the practitioner needs to utilize the removable lid during usage of the anchor device.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A catheter anchor device for use with a catheter which is inserted into a patient at a catheter insertion site for minimizing movement of the catheter that could result in pressure, discomfort, displacement, or tearing at the catheter insertion site, the catheter anchor device configured to automatically deploy one or more sutures to quickly and efficiently secure the catheter, the anchor device comprising:
    an adhesive layer configured to be secured to the skin of the patient proximate the catheter insertion site and having a center aperture surrounding the catheter insertion site that allows access to the catheter insertion site and permits a practitioner to view and clean the catheter insertion site without manipulating or removal of the adhesive layer;
    a rotatable ring secured to the adhesive layer while allowing access to the center aperture, the rotatable ring being actuatable by the user to secure the catheter relative to the catheter anchor device;
    one or more sutures coupled to the rotatable ring such that actuation of the rotatable ring actuates the one or more sutures to secure the catheter relative to the rotatable ring; and
    a ratchet mechanism utilized in connection with the rotatable ring, the ratchet mechanism allowing movement of the rotatable ring in a first direction while securing the rotational position of the rotatable ring against movement in a second direction.

2. The anchor device as recited in claim 1, wherein the ratchet mechanism includes a ratchet ring and a rotatable ratchet member.

3. The anchor device as recited in claim 2, wherein the rotatable ring comprises a base and a rotatable outer ring.

4. The anchor device as recited in claim 3, wherein the ratchet ring is secured to the base such that the base and the ratchet ring are fixed relative to the adhesive layer.

5. The anchor device as recited in claim 4, wherein the rotatable ratchet member is secured to the rotatable outer ring such that the rotatable ratchet member and the rotatable outer ring rotate relative to the base and the ratchet ring.

6. The anchor device as recited in claim 5, wherein the ratchet ring includes a plurality of teeth and the rotatable ratchet member includes one or more teeth which cooperatively interact to provide ratcheting of the rotatable ratchet member relative to the ratchet ring.

7. The anchor device as recited in claim 6, wherein the plurality of teeth of the ratchet ring allow for rotation of one or more teeth of the rotatable ratchet member in one direction while impeding rotation of the one or more teeth of the rotatable ratchet member in the opposite direction.

8. The anchor device as recited in claim 5, wherein rotation of the rotatable ratchet member and rotatable outer ring occurs pursuant to actuation of the one or more sutures.

9. The anchor device as recited in claim 8, wherein the ratchet mechanism secures the tension on the one or more sutures subsequent to actuation of the rotatable ring and actuation of the one or more sutures to secure the catheter.

10. A catheter anchor device for use with a catheter which is inserted into a patient at a catheter insertion site for minimizing movement of the catheter that could result in pressure, discomfort, displacement, or tearing at the catheter insertion site, the catheter anchor device configured to automatically deploy one or more sutures to quickly and efficiently secure the catheter, the anchor device comprising:
    an adhesive layer configured to be secured to the skin of the patient proximate the catheter insertion site and having a center aperture surrounding the catheter insertion site that allows access to the catheter insertion site and permits a practitioner to view and clean the catheter insertion site without manipulating or removing the adhesive layer;
    a rotatable ring secured to the adhesive layer while allowing access to the center aperture, the rotatable ring being actuatable by the user to secure the catheter relative to the catheter anchor device, wherein the rotatable ring comprises:
        a stationary base secured to the adhesive layer;
        a rotatable outer ring circumscribing the stationary base such that the rotatable outer ring can be rotated by the user relative to the stationary base; and
        a bearing member being positioned between the stationary base and the rotatable outer ring and having bearing properties facilitating rotation of the rotatable outer ring relative to the stationary base; and
    one or more sutures coupled to the rotatable ring such that actuation of the rotatable ring actuates the one or more sutures to secure the catheter relative to the rotatable ring.

11. The catheter anchor device as recited in claim 10, wherein the bearing member reduces friction resulting from rotation of the rotatable ring to facilitate rotation of the rotatable outer ring relative to the stationary base.

12. The catheter anchor device as recited in claim 10, wherein the bearing member reduces friction between the rotatable outer ring and the stationary base during rotation of the rotatable outer ring.

13. The catheter anchor device as recited in claim 10, wherein the bearing member comprises a solid surface bearing material.

14. The catheter anchor device as recited in claim 13, wherein the solid surface earing material includes a surface having one or more contact surfaces having a low coefficient of friction.

15. The catheter anchor device as recited in claim 10, wherein the bearing member comprises a roller bearing mechanism.

16. The catheter anchor device as recited in claim 10, wherein the bearing member utilizes a fluid bearing mechanism to reduce friction resulting from rotation of the rotatable ring.

17. The catheter anchor device as recited in claim 10, wherein the bearing member comprises a lubricant.

18. The catheter anchor device as recited in claim 10, wherein the bearing member is utilized in connection with a lubricant.

19. The catheter anchor device as recited in claim 10, wherein the bearing member is secured to the rotatable outer ring such that rotation of the rotatable outer ring results in rotation of the bearing member relative to the stationary base.

20. The catheter anchor device as recited in claim 10, wherein the bearing member comprises a plurality of bearing members.

21. The catheter anchor devices as recited in claim 20, wherein the plurality of bearing members comprise segments that do not extend along the entire outer a circumference of the stationary base.

22. A catheter anchor device for use with a catheter which is inserted into a patient at a catheter insertion site for minimizing movement of the catheter that could result in pressure, discomfort, or tearing at the catheter insertion site, the catheter anchor device configured to automatically deploy one or more sutures to quickly and efficiently secure the catheter, the anchor device comprising:
    an adhesive layer configured to be secured to the skin of the patient proximate the catheter insertion site and having a center aperture surrounding the catheter insertion site that allows access to the catheter insertion site and permits a practitioner to view and clean the catheter insertion site without manipulating or removing the adhesive layer;
    a rotatable ring secured to the adhesive layer while allowing access to the center aperture, the rotatable ring being actuatable by the user to secure the catheter relative to the catheter anchor device; and
    one or more sutures coupled to the rotatable ring such that actuation of the rotatable ring actuates the one or more sutures to secure the catheter relative to the rotatable ring.

23. The catheter anchor device as recited in claim 22, wherein the rotatable ring comprises a saddle, the saddle being configured to accommodate the catheter and minimize exposure of the catheter above an upper surface of the rotatable ring.

24. The catheter anchor device as recited in claim 23, wherein the one or more sutures secure the catheter at a plurality of positions along the length of the catheter.

25. The catheter anchor device as recited in claim 24, wherein the one or more sutures secure the catheter at three or more positions along the length of the catheter.

26. The catheter anchor device as recited in claim 24, wherein the one or more sutures secure the catheter at a point adjacent a catheter insertion site and a point adjacent the rotatable ring.

27. The catheter anchor device as recited in claim 22, wherein the one or more sustures comprise a first suture and a second suture, the first suture and the second suture configured to be actuated by actuation of the rotatable ring.

28. The catheter anchor device as recited in claim 27, wherein each of the first suture and the second suture provide a plurality of points of securement relative to the rotatable ring to minimize twisting, pulling, or other manipulation of the catheter relative to the catheter anchor device.

29. A catheter anchor device configured to automatically deploy one or more sutures to secure a catheter, the anchor device comprising:
    an adhesive layer configured to be secured to a patient;
    a deployment means for automatically securing a catheter; and
    at least one suture utilized in connection with the deployment means wherein actuation of the deployment means automatically deploys the at least one suture and secures the catheter relative to the anchor device.

30. A catheter anchor device as recited in claim 29, deployment means comprises a securement mechanism.

31. The catheter anchor device as recited in claim 30, wherein the securement mechanism comprises a base portion and a movable portion.

32. The catheter anchor device as recited in claim 31, wherein movement of the movable portion relative to the base portion automatically deploys the at least one suture.

33. The catheter anchor device as recited in claim 32, wherein the deployment means comprises a resilient pocket, such that the at least one suture are positioned in the resilient pocket.

34. The catheter anchor device as recited in claim 33, wherein the at least one suture is secured to a securement mechanism on one end and secured to itself on an opposing end inside a resilient pocket such that as the one end is moved, the corresponding at least one suture is configured to deploy from the one or more resilient pockets, and slidably tighten about a catheter positioned inside a central aperture of the anchor device.

35. The catheter anchor device as recited in claim 34, wherein the securement mechanism comprises a bearing member such that rotation of the bearing member is configured to deploy the at least one suture from the one or more resilient pockets.

36. The catheter anchor device as recited in claim 29, wherein the deployment means comprises a rotatable ring.

37. The catheter anchor device as recited in claim 36, the rotatable ring is wider than its height to minimize kinking of the catheter tube and to relieve pressure when pressed between the patient and a support surface.

38. The catheter anchor device as recited in claim 36, wherein the rotatable ring includes a plurality gripping members utilized to facilitate gripping and rotation of the rotatable ring.

39. The catheter anchor device as recited in claim 38, wherein the plurality of gripping member comprise scallops positioned on the outer circumference of the rotatable ring.

40. The catheter anchor device as recited in claim 29, further comprising a removable lid.

41. The catheter anchor device as recited in claim 40, wherein the removable lid is adapted to cover the catheter insertion point to prevent injury or infection of the catheter insertion point.

42. A catheter anchor device for use with a catheter which is inserted into a patient at a catheter insertion site for minimizing movement of the catheter that could result in pressure, discomfort, displacement, or tearing at the catheter insertion site, the catheter anchor device configured to automatically deploy one or more sutures to quickly and efficiently secure the catheter, the anchor device comprising:
    a securement base having a center aperture and being adapted to be secured to a patient in a manner to allow access to a catheter insertion site allowing access to the center aperture, a rotatable ring being actuatable by the user to secure the catheter relative to the catheter anchor device;

one or more sutures coupled to the securement base being actuatable by the user to secure the catheter relative to the securement base.

43. The catheter anchor device of claim 42, wherein the sutures are automatically deployable.

44. The catheter anchor device of claim 43, wherein the securement base includes a rotatable ring that automatically deploys the one or more sutures when a user rotates the rotatable ring.

* * * * *

UNITED STATES PATENT AND TRADEMARK OFFICE
CERTIFICATE OF CORRECTION

PATENT NO. : 7,470,256 B2  
APPLICATION NO. : 11/198666  
DATED : December 30, 2008  
INVENTOR(S) : Fred P. Lampropoulos et al.

Page 1 of 2

It is certified that error appears in the above-identified patent and that said Letters Patent is hereby corrected as shown below:

Column 1, Line 9 reads, "...'Self-suturing Anchor Device a Catheter'..." which should read, "...'Self-suturing Anchor Device for a Catheter'..."

Column 6, Line 37 reads, "...*b* do no contact the teeth..." which should read, "...*b* do not contact the teeth..."

Column 8, Line 12 reads, "...within the stuture..." which should read, "...within the suture..."

Column 8, Line 26 reads, "...within the stuture..." which should read, "...within the suture..."

Column 9, Line 36 reads, "...the outer circumference the base of..." which should read, "...the outer circumference at the base of..."

Column 12, Line 58 reads, "...solid surface earing material..." which should read, "...solid surface bearing material..."

Column 13, Line 13 reads, "The catheter anchor devises as recited in..." which should read, "The catheter anchor device as recited in..."

Column 13, Line 15 reads, "...the entire outer a circumference of..." which should read, "...the entire outer circumference of..."

Column 14, Line 8 reads, "A catheter anchor device as recited in claim 29, deployment..." which should read, "A catheter anchor device as recited in claim 29, wherein the deployment..."

Signed and Sealed this  
Fifteenth Day of March, 2011

David J. Kappos  
*Director of the United States Patent and Trademark Office*

CERTIFICATE OF CORRECTION (continued)
U.S. Pat. No. 7,470,256 B2

Column 14, Line 19 reads, "...at least one structure are positioned..." which should read, "...at least one structure is positioned..."

Column 14, Line 36 reads, "The catheter anchor device as recited in claim 36, the rotatable..." which should read, "The catheter anchor device as recited in claim 36, wherein the rotatable..."

Column 14, Line 41 reads, "...includes a plurality gripping members..." which should read, "...includes a plurality of gripping members..."

Column 14, Line 46 reads, "...the plurality of gripping member comprise..." which should read, "...the plurality of gripping members comprise..."